(12) United States Patent
Jahns et al.

(10) Patent No.: US 12,121,599 B2
(45) Date of Patent: Oct. 22, 2024

(54) FLUORESCENT GLAZING COMPOSITION FOR A DENTAL ZIRCONIA ARTICLE, PROCESS OF SINTERING AND KIT OF PARTS

(71) Applicant: 3M INNOVATIVE PROPERTIES COMPANY, St. Paul, MN (US)

(72) Inventors: Michael Jahns, Gilching (DE); Jacqueline C. Rolf, River Falls, WI (US); Martin Goetzinger, Pflugdorf (DE); Holger Hauptmann, Sindelsdorf (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 739 days.

(21) Appl. No.: 17/273,048

(22) PCT Filed: Aug. 30, 2019

(86) PCT No.: PCT/IB2019/057355
§ 371 (c)(1),
(2) Date: Mar. 3, 2021

(87) PCT Pub. No.: WO2020/049432
PCT Pub. Date: Mar. 12, 2020

(65) Prior Publication Data
US 2021/0196579 A1    Jul. 1, 2021

(30) Foreign Application Priority Data

Sep. 4, 2018 (EP) ..................... 18192447

(51) Int. Cl.
| A61K 6/822 | (2020.01) |
| A61K 6/20 | (2020.01) |
| A61K 6/833 | (2020.01) |
| A61K 6/836 | (2020.01) |
| C03C 1/04 | (2006.01) |
| C03C 4/00 | (2006.01) |
| C03C 4/12 | (2006.01) |
| C03C 8/20 | (2006.01) |
| C03C 10/00 | (2006.01) |
| C04B 41/86 | (2006.01) |

(52) U.S. Cl.
CPC .............. *A61K 6/822* (2020.01); *A61K 6/20* (2020.01); *A61K 6/833* (2020.01); *A61K 6/836* (2020.01); *C03C 1/04* (2013.01); *C03C 4/0021* (2013.01); *C03C 4/12* (2013.01); *C03C 8/20* (2013.01); *C03C 10/0009* (2013.01); *C03C 2204/00* (2013.01); *C03C 2205/06* (2013.01); *C04B 41/86* (2013.01)

(58) Field of Classification Search
CPC .......... A61K 6/822; A61K 6/20; A61K 6/836; A61K 6/833; C04B 41/86; C03C 1/04; C03C 4/04; C03C 4/0021; C03C 4/12; C03C 8/20; C03C 10/009; C03C 2204/00; C03C 2205/06
See application file for complete search history.

(56) References Cited

U.S. PATENT DOCUMENTS

| 7,985,119 | B2 | 7/2011 | Basler |
| 8,141,217 | B2 | 3/2012 | Gubler |
| 8,685,278 | B2 | 4/2014 | Yamada |
| 9,090,511 | B2 | 7/2015 | Rothbrust |
| 2004/0081765 | A1 | 4/2004 | Pitts |
| 2005/0064369 | A1 | 3/2005 | Zel |
| 2008/0241551 | A1 | 10/2008 | Zhang |
| 2010/0221683 | A1 | 9/2010 | Franke |
| 2013/0059272 | A1 | 3/2013 | Jahns |
| 2013/0149433 | A1* | 6/2013 | Ehrt ................. C04B 35/62665 427/2.29 |
| 2017/0143456 | A1 | 5/2017 | Carden |

FOREIGN PATENT DOCUMENTS

| CN | 105503274 | * | 4/2016 |
| DE | 20316004 | | 3/2004 |
| DE | 102015204109 | | 9/2016 |
| JP | 2005041825 | | 2/2005 |
| WO | WO 2001-13862 | | 3/2001 |
| WO | WO 2002-45614 | | 6/2002 |
| WO | WO 2010-062541 | | 6/2010 |
| WO | WO 2016-142234 | | 9/2016 |
| WO | WO 2017-144644 | | 8/2017 |

OTHER PUBLICATIONS

International Search Report for PCT International Application No. PCT/IB2019/057355, mailed on Jan. 2, 2020, 5 pages.

* cited by examiner

*Primary Examiner* — C Melissa Koslow

(57) ABSTRACT

The invention relates to a glazing composition for a porous dental zirconia article, the glazing composition comprising liquid, glass particles, fluorescing component(s) comprising europium, optionally hydrophilic silica nano-particles, and optionally hydrophobic silica nano-particles, wherein the fluorescing component(s) can be contained in the glass particles or as separate component. The invention also relates to a process for sintering a porous dental zirconia article with a glazing composition on its surface.

19 Claims, No Drawings

FLUORESCENT GLAZING COMPOSITION FOR A DENTAL ZIRCONIA ARTICLE, PROCESS OF SINTERING AND KIT OF PARTS

CROSS REFERENCE TO RELATED APPLICATIONS

This application is a national stage filing under 35 U.S.C. 371 of PCT/IB2019/057355, filed 30 Aug. 2019, which claims the benefit of European Patent Application No. 18192447.3, filed 4 Sep. 2018, the disclosure of which are incorporated by reference in their entireties herein.

FIELD OF THE INVENTION

The invention relates to a fluorescent glazing composition suitable for glazing the surface a dental zirconia article. The glazing composition comprises a liquid, glass particles, hydrophilic silica nano-particles and at least one Eu containing fluorescing component.

The invention also relates to a process for sintering a porous dental zirconia article with a glazing composition on its surface.

BACKGROUND

Currently, dental restorations are typically produced by using one of the following approaches:

One approach is to use an open-pored oxide ceramic, which can be machined in-office or chair-side.

However, after the milling step a time-consuming heat treatment step is needed for obtaining a high strength material. During the heat-treatment step e.g. a glass material is infiltrated into a porous ceramic article to improve the strength of the article.

Such a process is described e.g. in U.S. Pat. No. 9,090,511 (Rothbrust et al.). The infiltration of the infiltration substance into the pores of the open-pore oxide ceramic is typically done in vacuum and up to a depth of 2 to 90% of the thickness of the open-pore oxide ceramic. An infiltration depth in the range of 0.2 to 0.8 mm is reported.

Another approach is to grind fully sintered zirconia.

The strength level of fully sintered zirconia is higher compared to the strength of a glass ceramic material.

However, the esthetic is sometimes not considered fully satisfying and the grinding itself is time-consuming as well. Further, a glazing or polishing step is typically needed for obtaining the desired esthetic gloss.

Such an approach is described e.g. in US 2017/143456 A1 (Carden et al.), where a fully sintered zirconia material is milled into a dental restoration with a chair-side milling machine.

Another approach is to use a pre-sintered zirconia material.

The zirconia dental restoration is made in a dental laboratory by machining a pre-sintered (porous) block to a desired shape, thereby considering the shrinkage of the zirconia material during a later firing process.

After the firing step, a second so-called glaze-firing step is typically needed, particularly, if a glossy and highly aesthetic dental restoration is desired.

Further, the glazing of zirconia restorations is often recommended to reduce the risk of abrasion of the opposing tooth and because of esthetic reasons.

In this respect, glass powder is manually applied to the surface of the sintered zirconia material and both are fired at much lower temperature compared to the sintering temperature of the porous zirconia material. The glass powder typically melts at temperatures of less than 900° C.

There is also a desire for a highly aesthetic dental restoration.

Natural looking restorations show tooth-like fluorescence. Blue fluorescence is usually perceived as natural-looking or "tooth-like" fluorescence.

Except for the product Lava™ Esthetic (3M Oral Care), most of the dental zirconia materials on the market lack this feature.

If the dental zirconia material itself does not possess a fluorescence effect, the glaze can be used to compensate for the lack of fluorescence in the zirconia material. This is the most common solution currently used.

WO 2016/142234 A1 (Gebr. Brasseler) describes a substance mixture for finishing dental restorations of zirconium dioxide, comprising a so-called over-burnable lithium silicate system and/or feldspar system dispersed in an organic liquid. The heat-treatment is typically done at a temperature of 850 to 950° C. It is stated that the surface of the zirconium dioxide is preferably free of pores.

US 2008/0241551 A1 (Zhang et al.) suggests a method of preparing a functionally graded glass/zirconia/glass sandwich material comprising the steps of a) applying a certain powdered glass-ceramic composition to accessible surfaces of a pre-sintered zirconia substrate, b) infiltrating the glass-ceramic composition into the substrate; and c) densifying the substrate by heating. In the example section, glass-ceramic powder compositions are described which were used for infiltrating pre-sintered bodies of yttria-stabilized zirconia.

If such a process is applied to porous dental zirconia materials, the resulting article does not meet the requirements of an esthetic dental restoration.

WO 2010/062541 A1 (3M) relates to a dental article comprising zirconium oxide and at least two different coloring substances A and B, substance A showing a light emission in the range of 470 to 510 nm and substance B showing a light absorption in the range of 520 to 750 nm, the dental article being used as a dental support structure and not comprising glass or glass ceramic material in an amount above 10 wt. %.

U.S. Pat. No. 8,685,278 B2 (Yamada et al.) describes a fluorescent zirconia material including a fluorescent component and emitting fluorescence when excited with a light of a predetermined wavelength, the fluorescent component including a fluorescent material, the fluorescent material including at least one component of $Y_2SiO_5$:Ce, $Y_2SiO_5$:Tb, (Y, Gd, Eu)$BO_3$, $Y_2O_3$:Eu, YAG:Ce, $ZnGa_2O_4$:Zn or $BaMgAl_{10}O_{17}$:Eu and the fluorescent material being capable of emitting the fluorescence when subjected to firing treatment at temperatures ranging from 1,300 to 1,600° C. under oxidizing environments.

US 2005/0064369 A1 (Zel et al.) relates to a dental restoration comprising one or more opaque layers covered by one or more other porcelain layers, the opaque layers being situated closer to the core than the other porcelain layers, wherein at least one of the opaque layers contains a fluorescent material, and wherein the one or more other porcelain layers are predominantly transparent and opalescent.

US 2013/049272 A1 (Jahns et al.) describes a dental article comprising two sections A and B, section A comprising zirconia in a certain amount, a stabilizer and a component X comprising Dy or Sm or Eu or mixtures thereof, section B comprising a glass, glass ceramic or composite material, section B being located above the upper surface portion of section A.

Described is also a kit of parts comprising part 1 and part 2. Part 1 typically comprises a zirconia dental mill blank, a stabilizer and component X, whereas part 2 typically comprises a glass, glass ceramic or composite material.

DE 10 2015 20419 A1 (Gebr. Brassler) relates to a sprayable veneering ceramic composition for zirconia dental restorations. The veneering ceramic composition comprises a disperse phase and a dispersion medium, wherein the disperse phase contains a pulverized glass-ceramic material. The glass-ceramic material is obtained by first producing a glass which is then transferred into a glass-ceramic. The glass-ceramic material may contain coloring or fluorescing components selected from oxides and fluorides of Fe, Sn, Ce, Mn, V, Cr, Pr, Tb, Nd, Sm, In, Eu, Dy or combinations thereof. The veneering ceramic composition is applied to a zirconia dental restoration and heated to a temperature of 840° C. to 950° C.

SUMMARY OF INVENTION

An issue observed when applying commercially available glazing compositions containing fluorescing pigments to the surface of a porous dental zirconia article and co-firing the porous dental zirconia article with the glazing composition is that the glazing composition has to withstand the high temperatures of the zirconia sintering process which can go to 1,500° C. or higher.

It has been observed that the state-of-the-art fluorescence pigments, which are usually added to glazes do not survive these temperature conditions and no fluorescence can be observed in the final glaze after firing.

Thus, there is a need for an improved glazing composition, in particular a glazing composition which can be used for glazing a porous dental zirconia article.

It would also be desirable to have a glazing composition which shows fluorescence after firing.

Ideally, the glazing composition and the porous dental zirconia article treated with the glazing composition should be easy to handle.

It would also be desirable, to have a glazing composition at hand which can be co-fired with the porous dental zirconia article to which it has been applied, even if high heating rates are applied.

One or more of these objects are addressed by the invention described in the present text and claims.

In one embodiment the present invention features a glazing composition for a dental zirconia restoration as described in the present text and claims. The glazing composition comprises liquid, glass particles, fluorescing component(s) comprising europium, wherein the fluorescing component(s) can be contained in the glass particles or as separate component, optionally hydrophilic silica nano-particles, and optionally hydrophobic silica nano-particles as described in the present text and claims.

A further embodiment of the invention is directed to a process of producing a dental zirconia restoration as described in the present text and claims. The process comprises the steps of providing a porous dental zirconia article, applying the glazing composition to at least a part of the surface of the porous dental zirconia restoration, sintering the porous dental zirconia article with the glazing composition on its surface to final density as described in the present text and claims.

A further embodiment of the invention is directed to the dental restoration obtainable or obtained by this process.

The invention is also related to kit of parts as described in the present text and claims. The kit of parts comprises the glazing composition as described in the present text and claims, and a dental zirconia mill blank suitable for producing a dental restoration, and optionally the following items alone or in combination: sintering aids, application device for the surface treating agent, a shade guide, polishing aids, a sintering oven.

Moreover, the invention features the use of fluorescing components as described in the present text and claims for producing a glazing composition or conducting a sintering process as described in the present text and claims.

Unless defined differently, for this description the following terms shall have the given meaning:

The term "dental article" means any article which is to be used in the dental field, especially for producing a dental restoration and parts thereof.

A dental article typically has a 3-dimensional inner and outer surface including convex and concave structures. Compared to other articles such as pottery or paving stones, a dental article is small and filigree. The thickness of the dental article can vary from very thin, e.g. at the edges and rims (below 0.1 mm) to considerably thick, e.g. in the biting area (up to 8 mm). Sections bridging the crown portions in dental bridges might have a thickness up to 20 mm.

The outer surface typically has an overall convex shape, whereas the inner surface typically has an overall concave shape.

Typically, the dental article described in the present text comprises or essentially consists after sintering of a polycrystalline ceramic material comprising yttrium stabilized $ZrO_2$.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons), monolithic dental restorations (i.e. restorations which do not need to be veneered) and parts thereof.

The surface of a tooth is not regarded a dental article.

A dental article should not contain components which are detrimental to the patient's health and thus free of hazardous and toxic components being able to migrate out of the dental article.

By "dental mill blank" is meant a solid block (3-dim article) of material from which a dental article, dental workpiece, dental support structure or dental restoration can and typically is to be machined in any subtractive process, e.g. aside from milling also by grinding, drilling etc.

A dental mill blank has a geometrically defined shape and comprises at least one flat surface. A so-called "free form surface" is not regarded as "geometrically defined". In this respect, the shape of a dental restoration (e.g. crown or bridge) itself is not regarded a dental mill blank.

"Zirconia article" shall mean a 3-dimensional article wherein at least one of the x,y,z dimensions is at least 5 mm, the article being composed of at least 80 or at least 90 or at least 95 wt. % zirconia.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in three-dimensional periodic pattern (i.e., has long range crystal structure as determined by X-ray diffraction). Crystal structures include tetragonal, monoclinic, cubic zirconia and mixtures thereof.

"Monolithic dental restoration" means a dental ceramic article onto the surface of which no facing or veneer has been attached. That is, the monolithic dental restoration is essentially composed of only one material composition. However, if desired, a thin glazing layer can be applied.

"Glass" means an inorganic non-metallic amorphous material which is thermodynamically an under-cooled liquid. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component as a glass former and a certain amount of intermediate and modifier oxides.

The porous ceramic dental material described in the present text does not contain a glass.

"Glass-ceramic" means an inorganic non-metallic material where one or more crystalline phases are surrounded by a glassy phase so that the material comprises a glass material and a ceramic material in a combination or mixture. It is formed as a glass, and then crystallize by a nucleation and crystallization heat treatment. Glass ceramics may e.g. refer to a mixture of lithium-, silicon-, and aluminium-oxides.

The porous dental material described in the present text does not contain a glass-ceramic.

"Littleton Softening Point" in glasses is the temperature at which the glass reaches a viscosity of $10^{7.6}$ P (Poise) (or $10^{6.6}$ Pa*s). It is the lower boundary of the working range in which a glass can change shape.

"Flow point" is the temperature at which the glass reaches a viscosity of $10^5$ P or $10^4$ Pa*s. This is the temperature at which the glass starts to flow and can be worked by pressing, blowing, or pulling. If desired, this viscosity is measurable with a rotating plate viscometer.

A "powder" means a dry bulk composed of a large number of fine particles that may flow freely when shaken or tilted.

A "particle" means a substance being a solid having a shape which can be geometrically determined. The shape can be regular or irregular. Particles can typically be analysed with respect to e.g. grain size and grain size distribution.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells or pores in the sample is assumed to be the remainder of the sample volume (100% minus the total volume of material).

A "porous material" refers to a material comprising a partial volume that is formed by voids, or pores in the technical field of ceramics.

Accordingly, an "open-celled" structure of a material sometimes is referred to as "open-pored" structure, and a "closed-celled" material structure sometimes is referred to as a "closed-pored" structure. A material having an open-celled or open-pored structure can be passed through by e.g. gases.

The "average connected pore diameter" means the average size of the open pores of a material.

The term "calcining" refers to a process of heating a solid material to drive off at least 90 percent by weight of volatile chemically bound components (e.g., organic components) (vs., for example, drying, in which physically bound water is driven off by heating). Calcining is done at a temperature below a temperature needed to conduct a pre-sintering step.

The terms "sintering" or "firing" are used interchangeably. A porous ceramic article shrinks during a sintering step. The sintering temperature to be applied depends on the ceramic material chosen. For $ZrO_2$ based ceramics a typical sintering temperature range is 1,100° C. to 1,550° C. If the sintering is done with high heating-rates, higher temperatures may be required. Sintering typically includes the densification of a porous material to a less porous material having a higher density.

A dental zirconia article is classified as "pre-sintered", if the dental zirconia article has been treated with heat (temperature range of 900 to 1,100° C.) for 1 to 3 h to such an extent that the raw breaking resistance of the dental ceramic measured according to the "punch on three ball test" (biaxial flexural strength test) of ISO 6872:2015 is within a range of 15 to 55 MPa or 20 to 50 MPa.

A pre-sintered dental ceramic usually has a porous structure and its density (usually about 3.0 $g/cm^3$ for an yttrium stabilized $ZrO_2$ ceramic) is less compared to a completely sintered dental ceramic framework (usually about 6.1 $g/cm^3$ for an yttrium stabilized $ZrO_2$ ceramic).

By "machining" is meant milling, grinding, cutting, carving, or shaping a material by a machine. Milling is usually faster and more cost effective than grinding. A "machinable article" is an article having a 3-dimensional shape and having sufficient strength to be machined.

The term "can be combusted without leaving residues" means that if about 200 mg of the component is heated up to a temperature of about 750° C. for about 1 min at ambient pressure, no visible (visible with the human eye) deposits can be found.

That is, the component either evaporates or can be burnt producing only gaseous components including carbon oxide and water.

This can be determined, if desired, e.g. by visually (with the human eye only) inspecting a final dental restoration obtained after a firing step. A greyish appearance of the dental restoration can be an indicator for a dental composition not fulfilling the above-mentioned feature. E.g., using a composition containing a compound with long carbon chains (e.g. a polymer with a carbon backbone) typically leads to a dental restoration having a greyish appearance, which is not desirable.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component, if the composition does not contain said component as an essential feature. Thus, said component is not willfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

The terms "comprise" or "contain" and variations thereof do not have a limiting meaning where these terms appear in the description and claims. The term "comprise" shall include also the terms "consist essentially of" and "consists of".

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

"And/or" means one or both. E.g., the expression component A and/or component B refers to a component A alone, component B alone, or to both component A and component B.

DETAILED DESCRIPTION

It has been found that the glazing composition described in the text has a couple or number of advantageous properties.

The glazing composition is easy to apply and use.

Further, the glazing composition still shows fluorescence, even if it has been subject to a heat-treatment of 1,500° C. or higher.

The fluorescence provided by the glazing composition is similar to the fluorescence of a natural looking tooth.

Without wishing to be bound to a certain theory, it is believed that certain rare earth elements such as Eu (optionally supported by addition of Dy) can also provide a blue fluorescence in glass materials.

In that case, no additional fluorescing pigments are needed. It is sufficient, if only the ions of these elements are somehow dissolved or contained in the glass matrix.

This is surprising as the addition of Eu to a zirconia material results in reddish fluorescence, which is typically not desirable from an esthetic point of view for dental materials. This approach is described in US 2013/0059272 A1 (Jahns et al.), where a component X comprising Dy, Sm, Eu or mixtures thereof is contained in a zirconia dental article.

Further, it was found that glazing composition as described in the present text has the necessary robustness to maintain the fluorescence effect even if high heating rates are applied.

The addition or use of a fluorescing agent as described in the present text, is especially useful for producing a glazing composition which can be used during a so-called "1-step firing process", i.e. a process where a porous dental zirconia article is sintered together with a glazing composition on its surface. This is in contrast to processes described in the art, where a glazing composition is applied to an already sintered dental zirconia article (as e.g. described in DE 10 2015 204 109 A1 (Gebr. Brasseler)). Further, adding the fluorescing component(s) described in the present text to a glazing composition instead of implementing the fluorescing component(s) into the ceramic matrix of a dental zirconia restoration is beneficial for the practitioner as he can then freely choose which dental zirconia material he wants to use.

The glazing composition described in the present text is suitable for glazing a dental zirconia restoration.

The glazing composition comprises a liquid.

The liquid is used for dispersing or dissolving the components contained in the glazing composition and may be used for adjusting the viscosity and consistency of the composition according to the practitioner's needs.

The nature of the liquid is not particularly limited, unless the desired effect cannot be achieved.

The liquid is typically a polar liquid. A polar liquid is a liquid which is miscible with water.

Typically, suitable liquids can be characterized by at least one of the following features:
  molecular weight (Mw): from 18 to 1,000 g/mol or from 40 to 400 g/mol;
  boiling point: 50 to 300° C.;
  viscosity: 1 to 2,000 mPa*s or 1 to 1,500 mPa*s (measured at 23° C. at a shear rate of 50 s-1);
  free of polymerizable groups like (meth)acrylate groups, epoxy groups, carbon-carbon unsaturated groups;
  not containing elements selected from S and P.

Mw (substance) is the average molecular weight of the respective polymer used.

The liquid should have a boiling point allowing the liquid to evaporate during the fast firing process without complications, or during a drying step which is optionally carried out before the firing process is started.

The boiling point of the liquid should not be too high. Otherwise the evaporation of the liquid during the firing process might not be sufficiently fast. Evaporation of the liquid should be finished before the glass material starts to melt and flow.

The boiling point of the liquid may also be adjusted by using liquids having a suitable molecular weight.

It is beneficial, if the viscosity of the liquid is such that the glass powder can easily be dispersed.

The liquid should not contain components or chemical elements which may cause damage to the sintering furnace used for the fast firing process.

Using liquids which do not contain halogen components (e.g. F, Cl, Br) is sometimes preferred.

Solvents which can be used include water or polyalcohols including ethylene glycol, polyethylene glycols, glycerol and mixtures thereof.

Polyethylene glycols which can be used can be represented by the following formula

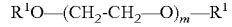

$R^1O-(CH_2-CH_2-O)_m-R^1$ with $R^1$=H, acyl, alkyl, aryl, alkylaryl, polypropylglycol, poly-THF, preferably H, acetyl, methyl, ethyl, propyl, butyl, hexyl, octyl, nonyl, decyl, lauryl, tridecyl, myristyl, palmityl, stearyl, oleyl, allyl, phenyl, p-alkylphenyl, polypropyleneglycol, poly-THF and m=2 to 20, preferably 2 to 15, more preferably 2 to 8.

The average molecular weight (Mw) of the polyethylene glycol should be in the range of 100 to 1,000, preferably in the range of 100 to 700, more preferably in the range of 100 to 400.

If desired, the average molecular weight (Mw) can be determined according to procedures known to a person skilled in the art as described for example in Arndt/Miller, Polymercharakterisierung, Hanse Verlag, 1996.

Most PEGs (polyethylene glycols) include molecules with a distribution of molecular weights, i.e. they are polydisperse. The size distribution can be characterized statistically by its weight average molecular weight (Mw) and its number average molecular weight (Mn), the ratio of which is called the polydispersity index (Mw/Mn). Mw and Mn can be measured by mass spectroscopy.

Specific examples of water-miscible liquid, which can be used, include polyol(s) (including polyvinyl alcohol), glycol ether(s) (e.g. diethylene glycol methyl ether, diethylene glycol ethyl ether), alcohol(s) (including 1,2-propanediol, 1,3-propanediol, ethanol, (n- and iso-)propanol, glycerol), glycerol ether, and mixtures thereof.

Specific examples of polyethylene glycol which can be used include PEG 200, PEG 285-315, PEG 380-420, PEG 570-630, PEG 950-1050.

In particular, the following solvents were found to be useful: water, glycerol, ethylene glycol, propylene glycol and mixtures thereof.

The water can be distilled, de-ionized, or plain tap water. Typically, de-ionized water is used.

According to one embodiment, the solvent is water. According to another embodiment, the solvent is different from water.

The liquid is typically present in the following amounts:
Lower amount: at least 50 or at least 60 wt. %;
Upper amount: at most 95 or at most 90 wt. %,
Range: 50 to 95 or 60 to 90 wt. %,
wt. % with respect to the amount of the whole composition.

The glazing composition described in the present text comprises glass particles.

The nature and composition of the glass particles is not particularly limited, unless the desired object cannot be achieved Suitable glasses can be described by the following features alone or in combination:
a) viscosity: at least $10^4$ Pa*s at a temperature of 1,300° C.;
b) coefficient of thermal expansion: $1*10^{-6}$ $K^{-1}$ to $10*10^{-6}$ $K^{-1}$ or $2.5*10^{-6}$ $K^{-1}$ to $9*10^{-6}$ $K^{-1}$;
c) surface tension: of 210 to 300 mN/m at 1,300° C.;
d) Littleton softening point viscosity at a temperature of 1,100° C. to 1,350° C.;
e) flow point viscosity at a temperature of 1,300° C. to 1,650° C.;
f) particle size: 1 to 40 μm ($D_{50}$).

A combination of the following features is sometimes preferred: a) and b); a) and c); a) and d); a) and f); a) and e); a), b) and c); a), b) and d); a), b) and e); a), b), d) and f).

The glass typically has a sufficiently high viscosity at the sintering temperature of the porous dental zirconia article, so that the glass does not migrate into the pores of the porous zirconia dental article to a degree more than what is desired. A viscosity range in the above-mentioned range was found to be useful.

It can be beneficial, if the value of the coefficient of thermal expansion of the glass is smaller than the thermal expansion of the zirconia material. This may help to increase the compressive strength of the final dental restoration and might facilitate the provision of a durable dental restoration.

The particle size of the glass particles should not be too large as this may negatively influence the melting behavior during the sintering process.

Using smaller glass particles typically allow for a more homogenous melting of the glass during the sintering process.

Ideally, the particle size of the glass powder is in a range which allows homogenous melting of the glass powder during the sintering process of the porous zirconia dental article.

The $D_{50}$ particle size is typically in the range of 1 to 40 μm or 2 to 30 μm. The size of the particles is typically in a range of 0.1 μm to 50 μm or 0.25 μm to 40 μm.

If desired, the particle size and viscosity, can be determined or obtained as described in the example section.

The glass is typically a silica-based glass. The $SiO_2$ content of the glass is typically above 80 wt. %, and preferably in a range of 80 to 98 wt. %.

According to one embodiment, the glass is characterized by comprising either of the following compositions:

| | | | | | | | |
|---|---|---|---|---|---|---|---|
| $SiO_2$ | 80 to 98 | 80 to 98 | 80 to 98 | 80 to 98 | 80 to 98 | 85 to 98 | 80 to 98 |
| $B_2O_3$ | 0 to 15 | 0 to 15 | 2 to 15 | | | 2 to 15 | |
| $Na_2O$ | 0 to 5 | 0 to 5 | | | | | |
| $K_2O$ | 0 to 5 | 0 to 5 | | 0.1 to 5 | 0.1 to 5 | | 5 to 10 |
| $Al_2O_3$ | 0 to 5 | 0 to 5 | 0.1 to 5 | 0.1 to 5 | 0.1 to 5 | | 8 to 12 |
| $La_2O_3$ | 0 to 1 | 0 to 1 | | | | | |
| MgO | 0 to 5 | 0 to 5 | | 0.1 to 5 | 0.1 to 5 | | |
| CaO | 0 to 2 | 0 to 2 | | | | | |
| SrO | 0 to 2 | 0 to 2 | | | | | |
| BaO | 0 to 2 | 0 to 2 | | | | | |
| $Bi_2O_3$ | 0 to 0.5 | 0 to 0.5 | | | | | |
| $Eu_2O_3$ | 0 to 1 | 0.05 to 1 | | | | 0 to 1 | |

The amounts are given in mol % with respect to the glass composition.

The glass typically does not comprise the following components alone or in combination:
$Li_2O$ in an amount of more than 0.1 mol %;
F in an amount of more than 0.1 mol %;
$P_2O_5$ in an amount of more than 0.1 mol %.

The presence of these components may negatively affect properties like melting temperature range, surface tension, or viscosity of the glass.

The glass particles are typically present in the following amounts:
Lower amount: at least 5 or at least 8 wt. %;
Upper amount: at most 50 or at most 40 wt. %,
Range: 5 to 50 or 8 to 40 wt. %,
wt. % with respect to the amount of the whole glazing composition.

The glazing composition described in the present text comprises a fluorescing component.

The fluorescing component comprises europium (Eu) or a mixture of europium (Eu) and dysprosium (Dy), wherein europium (Eu) is sometimes preferred as the fluorescing effect caused by Eu can be more "tooth-like" than the fluorescing effect caused by the mixture. However, using a mixture can enable a "fine-tuning" of the fluorescence color.

The fluorescing components are typically provided in solid form.

According to one embodiment, the fluorescing component is present in particle form in the glazing composition.

A particle size in the range of 1 to 40 μm ($D_{50}$) was found to be suitable as it allows the preparation of a homogeneous paste. However, if desired, smaller particles can also be present.

Examples of fluorescing components in particle form include oxides, hydroxides, nitrates and carbonates of europium, including europium (III) oxide and mixtures of europium (III) oxide and dysprosium (III) oxide.

According to another embodiment, the fluorescing component is dissolved in the glass particles.

This can be achieved by adding the fluorescing component before or during the melting process of the glass, i.e. when the glass material is prepared.

If desired, also a mixture of particulate fluorescing components and fluorescing components dissolved or dispersed in the glass can be used.

It is assumed that during the firing process the fluorescing component(s) become dissolved as ions. These ions will be embedded in the glass structure of the glaze.

The fluorescing component(s) calculated with respect to the amount of europium are typically present in the following amounts:

Lower amount: at least 0.1 or at least 0.2 wt. %;
Upper amount: at most 5 or at most 4 wt. %,
Range: 0.1 to 5 or 0.2 to 4 wt. %, wt. % with respect to the amount of the whole composition.

The glazing composition described in the present text may also comprise hydrophilic silica nano-particles.

The nature of the hydrophilic silica nano-particles is not particularly limited, unless the desired object cannot be addressed.

It was found that the addition of a hydrophilic silica nano-particles to the glazing composition may help to improve the handling properties during and after application.

Even, if the liquid component(s) of the glazing composition are absorbed by the porous dental zirconia article, the remaining solid components, in particular the glass particles nevertheless remain sufficiently fixed to the surface of the porous dental zirconia article.

This effect can be observed, if e.g. hydrophilic silica nano-particles are used, but not if hydrophobic silica nano-particles are used. Hydrophobic silica nano-particles are typically surface treated, e.g. silanized.

If glass particles are used for glazing a porous dental zirconia article, sometimes the fired glaze has a slightly white haze or the surface finish is not as smooth as desired.

The undesired haze might be caused by a chemical separation effect during firing or the inclusion of air bubbles into the glaze layer.

Without wishing to be bound by a certain theory, it is believed that the hydrophilic silica nano-particles may help to obtain a better packing of the glaze particles during application, thus reducing the risk of possible air inclusions.

It might also be possible, that the binder component act as a lubricant between the glass particles contained in the glazing composition during firing and ensure a suitable surface finish.

It has been observed that the hydrophilic silica nano-particles may help to bind the glass particles to the surface of the porous dental zirconia article, even if the liquid used for dispersing the glass particles in the glazing composition has been absorbed by the porous dental zirconia article to which the glazing composition has been applied.

As a result, the treated outer surface of the porous dental zirconia article can be handled more easily. The risk of accidentally removing the applied layer of glass particles is reduced. This improves the robustness during handling prior to firing.

Surprisingly, it was also observed that the presence of hydrophilic silica nano-particles does not negatively affect the esthetics of the glaze, even if the melting temperature ranges of the silica particles and the glass of the glazing composition do not match perfectly.

With respect to certain embodiments, it was observed that the esthetics of the glaze can be even improved, if silica nano-particles are added to the glazing composition, in particular with regard to gloss and haze.

Thus, it was found that the addition or use of hydrophilic silica nano-particles can positively influence the properties of a dental glazing composition.

The hydrophilic silica nano-particles are typically non silanized, i.e. they have a surface which has not been treated with a silanization agent.

If desired, the hydrophilic silica nano-particles can be characterized by the following features alone or in combination:

a) BET surface: 20 to 500 $m^2/g$.
b) particle size: 10 to 70 nm ($D_{50}$).

Suitable hydrophilic silica nano-particles include pyrogenic silica or precipitated silica.

Non-silanized silica nano-particles which can be used are also commercially available. Examples include Aerosil™ OX 50; Aerosil™ 200, Aerosil™ 380, Sipemat™ 160 (Evonik), Levasil™ 50/50 (Akzo Nobel).

If present, the hydrophilic silica nano-particles are typically present in the following amounts:

Lower amount: at least 0.1 or at least 0.2 wt. %;
Upper amount: at most 5 or at most 4 wt. %,
Range: 0.1 to 5 or 0.2 to 4 wt. %, wt. % with respect to the amount of the whole composition.

Besides hydrophilic silica nano-particles, the glazing composition can also contain hydrophobic silica nano-particles.

Hydrophobic silica nano-particles are typically silanized with a hydrophobic surface treating agent.

If present, the amount of hydrophobic silica nano-particles is preferably adjusted such that the effect resulting from the non-silanized silica nano-particles is not overruled.

Thus, if present, the hydrophobic silica nano-particles are typically present in a lower amount compared to the hydrophilic silica nano-particles (e.g. less than 50 wt. %, or less than 40 wt. % or less than 30 wt. % or less than 20 wt. % of the amount of the hydrophilic silica nano-particles).

Silanized silica nano-particles which can be used are also commercially available. Examples include HDK™ H2000, HDK™ 1303VP, HDK™ H3004, HDK™ H15, HDK™ H20 HDK™ H30 (Wacker).

To distinguish between hydrophilic and hydrophobic silica nano-sized particles, the following test can be conducted:

To a small amount of silica nano-particles (e.g. 0.5 g) a small amount of water is added (e.g. 1 ml).

If the silica nano-particles are readily wetted by the water, the silica nano-particles are regarded as hydrophilic. Hydrophobic particles will typically not mix with the water and remain as a separate phase.

The glass powder to liquid ratio in the glazing composition is typically in a range of 1:1 to 1:15 or 1:2 to 1:12 by weight.

The ratio of hydrophilic silica nano-particles to glass particles is typically in a range of 1:40 to 1:5 or 1:30 to 1:10 with respect to weight.

The ratio of glass particles to europium is typically in a range of 1,000:1 to 20:1 with respect to weight.

Such ratios were found to be advantageous.

The glass powder to liquid ratio can be helpful for adjusting the coating properties of the glazing composition.

The hydrophilic silica nano-particles to glass particles ratio can be used for adjusting the handling properties.

The glazing composition described in the present text may further comprise a rheological additive. The rheologic additive is typically an organic additive.

Adding a rheological additive can sometimes be advantageous, as it may help to further improve the storage stability of the glazing composition and prevent settling or separation.

The rheological additive is selected such it can be combusted without leaving residues during a firing process.

Rheological additives which can be used or added include starch, methyl cellulose, ethyl cellulose, hydroxyl propyl cellulose, carboxy methyl cellulose, xanthan and mixtures thereof.

Xanthan gum is a polysaccharide. It can be produced by a process involving fermentation of glucose or sucrose using the bacterium *Xanthomonas campestris*. The backbone of the polysaccharide chain contains β-D-glucose units linked through the 1 and 4 positions. The side chain contains mannose and glucuronic acid. The overall chain consists of repeating modules of five sugar units. The molecular weight of xanthan typically varies within a range of 1 million up to 50 million depending upon how it is prepared.

It has been found that by adding xanthan gum to a liquid, typically an increase in its viscosity can be observed, even if added in only small quantities, e.g. on the order of 1 wt. %.

Methyl cellulose is a methyl ether of cellulose, arising from substituting the hydrogen atoms of some of cellulose's hydroxyl groups —OH with methyl groups —CH$_3$, forming —OCH$_3$ groups.

Hydroxy propyl cellulose is an ether of cellulose in which some of the hydroxyl groups in the repeating glucose units have been hydroxy-propylated forming —OCH$_2$CH(OH)CH$_3$ groups.

A rheological additive may be present in an amount of 0 to 1 wt. % with respect to the weight of the glazing composition.

If present, the rheological additive is typically present in the following amounts:
Lower amount: at least 0.1 or at least 0.2 wt. %;
Upper amount: at most 1 or at most 0.8 wt. %,
Range: 0.1 to 1 or 0.2 to 0.8 wt. %,
wt. % with respect to the amount of the whole composition.

The glazing composition described in the present text may further comprise a colorant.

Adding a colorant can be beneficial for enhancing the visibility of the glazing composition during use, especially if the surface treating agent is transparent or of the same colour as the zirconia milled restorations.

Thus, the practitioner can easily determine to which parts of the surface of the dental article the composition has already been applied and which parts have not been treated yet and/or should remain untreated. The colorants, which are typically of organic nature will be burnt out during a later sintering step and thus not be incorporated into the dental article.

Examples of soluble colorants which can be used include Riboflavin (E101), Ponceau 4R (E124), Green S (E142), Patent Blue V (E131).

A colorant may be present in an amount of 0 to 0.5 wt. % with respect to the weight of the glazing composition.

If present, the colorant is typically present in the following amounts:
Lower amount: at least 0.001 or at least 0.01 wt. %;
Upper amount: at most 0.5 or at most 0.2 wt. %,
Range: 0.001 to 0.5 or 0.01 to 0.2 wt. %,
wt. % with respect to the amount of the whole composition.

The glazing composition is typically provided to the practitioner in a form which allows a simple application of the glazing composition to the surface of the porous dental zirconia article.

A viscosity of the glazing composition in the range of 5 to 5,000 mPa*s (23° C.) or 10 to 2,500 mPa*s (23° C.) was found to be useful.

If the viscosity is either too high or too low, it will become more difficult to apply the glazing composition precisely. The thickness of the glazing layers might become either too thick or too thin or the liquid of the composition is absorbed into the porous zirconia too quickly or too slowly.

The pH value of the glazing composition is typically within a range of 6 to 9.

That is, the glazing composition is typically in the neutral or slightly basic range based on the glass particles used. It typically does not contain acidic components.

The glazing composition can be characterized by comprising the respective components in the following amounts:
liquid: 50 to 95 wt. %,
glass particles: 4 to 40 wt. %,
fluorescing component(s) calculated with respect to the amount of europium: 0.1 to 5 wt. %,
hydrophilic silica nano-particles: 0 to 5 wt. %,
hydrophobic silica nano-particles: 0 to 5 wt. %,
wt. % with respect to the weight of the whole composition.

The glazing composition can also be characterized by comprising the respective components in the following amounts:
liquid: 60 to 90 wt. %,
glass particles: 9 to 30 wt. %,
fluorescing component(s) calculated with respect to the amount of europium: 0.1 to 5 wt. %,
hydrophilic silica nano-particles: 0.1 to 4 wt. %,
hydrophobic silica nano-particles: 0 to 5 wt. %,
wt. % with respect to the weight of the whole composition.

The glazing composition described in the present text typically does not contain components which are detrimental to the object to be achieved.

As the glazing composition is intended to be used to be co-fired with a porous dental zirconia article, the glazing composition typically does not contain components, such as glasses, which have a low melting temperature range.

These glasses would start melting before the pores of the dental zirconia article close and thus diffuse into the surface area of the dental zirconia article to be sintered to an undesirable extent.

Thus, according to certain embodiments, the glazing composition described in the present text typically does not comprise the following components alone or in combination:
glass particles having the Littleton softening point viscosity at a temperature of 1,100° C. or below in an amount of more than 1 wt. %;
glass particles having a viscosity of $10^3$ Pa*s or below at 1,300° C. in an amount of more than 1 wt. %.

According to one embodiment, a suitable glazing composition comprises the following components:
liquid selected from water, alcohol and mixtures thereof in an amount of 50 to 95 wt. %,
glass particles in an amount of 4 to 50 wt. %,
the glass particles having a mean particle size of 1 to 30 μm;
the glass of the glass particles having a viscosity of $10^4$ to $10^7$ Pa*s at 1,300° C.,
fluorescing component(s) calculated with respect to amount of europium in an amount of 0.1 to 5 wt. %, wt. % with respect to the weight of the whole glazing composition,
wherein the fluorescing component(s) can be contained in the glass particles or as separate component.

According to a further embodiment, a suitable glazing composition comprises the following components:
liquid selected from water, alcohol and mixtures thereof in an amount of 60 to 95 wt. %,
glass particles in an amount of 4 to 40 wt. %,
the glass particles having a mean particle size of 1 to 30 μm;
the glass of the glass particles having a viscosity of $10^4$ to $10^7$ Pa*s at 1,300° C.,
fluorescing component(s) calculated with respect to amount of europium in an amount of 0.1 to 5 wt. %,
wt. % with respect to the weight of the whole glazing composition,
wherein the fluorescing component(s) can be contained in the glass particles or as separate component.

According to a further embodiment, a suitable glazing composition comprises the following components:
liquid selected from water, alcohol and mixtures thereof in an amount of 65 to 90 wt. %,
glass particles in an amount of 9 to 35 wt. %,
the glass particles having a mean particle size of 1 to 20 μm;
the glass of the glass particles having a viscosity of $10^4$ to $10^7$ Pa*s at 1,300° C.,
the glass being a silica-based glass,
a fluorescing component(s) calculated with respect to amount of europium in an amount of 0.1 to 5 wt. %,
hydrophilic silica nano-particles: 0.1 to 4 wt. %,
wt. % with respect to the weight of the whole glazing composition,
wherein the fluorescing component(s) can be contained in the glass particles or as separate component.

According to a further embodiment, a suitable glazing composition comprises the following components:
liquid selected from water, alcohol and mixtures thereof in an amount of 60 to 90 wt. %,
glass particles in an amount of 9 to 40 wt. %,
the glass particles having a mean particle size of 1 to 20 μm;
the glass of the glass particles having a viscosity of $10^4$ to $10^7$ Pa*s at 1,300° C.,
a fluorescing component(s) calculated with respect to amount of europium in an amount of 0.1 to 5 wt. %,
wherein the fluorescing component(s) can be contained in the glass particles or as separate component,
hydrophilic silica nano-particles: 0.1 to 4 wt. %,
wt. % with respect to the weight of the whole glazing composition,
the glass comprising either of the following compositions:

| | | | | | | |
|---|---|---|---|---|---|---|
| $SiO_2$ | 80 to 98 | 80 to 98 | 80 to 98 | 80 to 98 | 85 to 98 | 80 to 98 |
| $B_2O_3$ | 0 to 15 | 0 to 15 | 2 to 15 | | 2 to 15 | |
| $Na_2O$ | 0 to 5 | 0 to 5 | | | | |
| $K_2O$ | 0 to 5 | 0 to 5 | | 0.1 to 5 | | 5 to 10 |
| $Al_2O_3$ | 0 to 5 | 0 to 5 | 0.1 to 5 | 0.1 to 5 | | 8 to 12 |
| $La_2O_3$ | 0 to 1 | 0 to 1 | | | | |
| MgO | 0 to 5 | 0 to 5 | | 0.1 to 5 | | |
| CaO | 0 to 2 | 0 to 2 | | | | |
| SrO | 0 to 2 | 0 to 2 | | | | |
| BaO | 0 to 2 | 0 to 2 | | | | |
| $Bi_2O_3$ | 0 to 0.5 | 0 to 0.5 | | | | | wherein the amounts are given in mol % with respect to the glass composition.

The glazing composition described in the present text can be obtained by mixing the respective components. If desired, the mixing can be done by using a speed mixing device or blender.

The glazing composition described in the present text is typically provided to the practitioner in a suitable receptacle, e.g. a vessel, bottle, tube, or flask.

The glazing composition described in the present text can be provided as dispersion, paste or spray.

The invention also relates to a process of producing a dental zirconia restoration by sintering a porous dental zirconia article.

Such a process comprises the steps of
providing a porous dental zirconia article,
applying the glazing composition described in the present text to at least a part of the surface of the porous dental zirconia restoration,
sintering the porous dental zirconia article with the glazing composition on its surface to final density.

The glazing composition is applied to at least a part of the surface of the porous dental zirconia article to be sintered. The porous dental zirconia article is in dry state.

If the porous dental zirconia article has the shape of a dental restoration, the article has an outer surface (which remains visible in the patient's mouth) and an inner surface (which becomes invisible, once the dental restoration has been fixed to the remaining tooth structure).

The glazing composition is applied to the outer surface of the porous dental zirconia article.

The glazing composition is typically applied at least to those parts of the outer surface of the porous dental zirconia restoration, which remain visible in the mouth of a patient after the sintered dental zirconia restoration has been fixed to the tooth structure of the patient.

Typically, the glazing composition is applied to at least 30% or at least 50% or at least 70% of or at least 90% of the outer surface of the porous dental zirconia restoration.

The glazing composition is typically not applied to the inner surface of the porous dental zirconia restoration.

A glazing composition on the inner surface may be detrimental for a later fixation process (e.g. cementing step) of the sintered dental zirconia restoration to a tooth surface.

Thus, the inner surface of the porous dental restoration is not treated with the glazing composition to an extend which would negatively affect such a fixation process.

The application of the glazing composition is typically done with a suitable application instrument. Suitable application instruments are described later in the text.

E.g., the application of the surface treating agent can be done by brushing or by spraying.

This is particularly feasible, if the glazing composition is provided as dispersion of a glass powder in a liquid.

The liquid of the glazing composition may be evaporated before a firing step is conducted. Thus, before the sintering process is started, optionally a drying step is conducted.

In a next step, a firing step of the porous dental zirconia article with the glazing composition comprising a glass on its outer surface is conducted.

During the firing process, the porous dental article is sintered to its final shape, thereby undergoing changes with regard to dimension, density, hardness, bending strength and/or grain size.

The firing step should be accomplished under conditions which results in a dental ceramic restoration having an acceptable tooth like colour (e.g. a colour which fits into the Vita™ shade guide).

The porous dental zirconia article to be sintered is typically produced as follows:

A porous dental mill blank is provided. The porous dental mill blank is machined to obtain a porous zirconia dental article.

The machining step can be done with a milling, drilling, cutting, carving, or grinding device.

Those devices are commercially available e.g. from Roland (DWX mills), or Sirona (CEREC™ inLab CAD/CAM) or others.

If the machining is done by milling, useful milling parameters include:

rotary speed of milling tool: 5,000 to 40,000 revolutions/min;
feed rate: 20 to 5,000 mm/min;
milling cutter diameter: 0.8 to 4 mm.

If desired, the machined porous dental zirconia restoration is cleaned, e.g. removing milling dust with pressurized air.

As the porous dental zirconia mill blank is used for producing the porous dental zirconia article, the material of the porous dental zirconia mill blank is the same as the material of the porous dental zirconia article.

The porous dental zirconia mill blank has typically the shape of a block or disc.

If the porous dental zirconia mill blank has the shape of a block, the porous zirconia dental mill blank has typically the following dimensions:

x-dimension: 12 to 45 mm, or 15 to 40 mm,
y-dimension: 12 to 70 mm, or 15 to 60 mm,
z-dimension: 10 to 30 mm, or 15 to 25 mm.

If the porous dental zirconia mill blank has the shape of a disc, the porous dental zirconia mill blank has typically the following dimensions:

x, y-dimension: 90 to 110 mm, or 95 to 105 mm,
z-dimension: 5 to 35 mm, or 10 to 30 mm.

Attaching or fixing the dental zirconia mill blank to a machining device, especially to the clamping appliance(s) of such a device, can also be accomplished by providing the blank with suitable means therefore.

Suitable means include frame(s), notch(es), stub(s), mandrel(s) and combinations thereof.

In another embodiment, the dental zirconia mill blank is fixed to or contained in a holding device. The holding device containing the dental mill blank may then function as a means for attaching the blank to a machining device.

Fixing of the dental zirconia mill blank to a holding device can be affected by clamping, gluing, screwing and combinations thereof.

Useful holding devices include frames (open and closed), stubs or mandrels. Using a holding device may facilitate the production of the dental article with a machining device.

Examples of useful holding devices are described in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

The porous zirconia mill blank can be produced as follows:

The porous zirconia material of the dental mill blank can be obtained by a process comprising the steps of mixing the powders of the respective oxides contained in the material to obtain a powder mixture and pressing the powder mixture.

Mixing of the oxide powders can be achieved by shaking the powders or putting the powders in a mill (e.g. ball mill) and milling the powders until a homogenous powder mixture is obtained. Further possible mixing equipment can include sieves or granulators.

To facilitate the pressing step(s), pressing aids can be added, if desired.

Suitable pressing aids include binders, lubricating additives and mixtures thereof.

If desired, these aids can be added to the zirconia oxide powder being the main component of the powder mixture.

Suitable metal oxide powders are commercially available from various sources including Tosoh Company (Japan).

The powder mixture is then placed in a mould and pressed into the shape of a dental mill blank.

The applied pressure is typically in a range of 150 to 300 MPa. Alternatively, the applied pressure is set so that the pressed ceramic body reaches a certain density, e.g. in the case of a zirconia ceramic a density from 2.8 g/cm$^3$ to 3.5 g/cm$^3$ or 2.85 g/cm$^3$ to 3.35 g/cm$^3$.

The article obtained after pressing the powder mixture can be machined or sliced into any desired shape.

If desired, a calcining step can be done.

In a further step, a heat treatment is applied to the compacted composition to obtain a porous dental mill blank.

The temperature of the heat treatment is typically within a range of 800 to 1,100° C. or 900 to 1,000° C.

The heat treatment is typically applied for a duration of 30 to 70 hours or 35 to 60 hours.

The porous zirconia dental mill blank is typically provided to the customer in a form allowing the mounting of the dental mill blank in a milling machine.

Either the top or bottom surface of the porous zirconia dental mill blank typically contains a marking element (e.g. printing or carving) which facilitates the correct orientation of the dental mill blank in a milling machine.

The porous dental zirconia article to be sintered can typically be characterized by the following parameters alone or in combination:

a) density: from 2.85 to 3.35 g/cm$^3$;
b) BET surface: 5 to 12 m$^2$/g or from 5.5 to 11 m$^2$/g.

Using a porous dental zirconia article having a BET surface in the above-mentioned range can be advantageous, because it ensures an adequate sintering activity of the material before and during the heat-treating process, in particular during the first heat-treating step with a high heating rate.

An adequate sintering activity is typically needed for obtaining a zirconia article showing the desired translucency within a short sintering time.

Without wishing to be bound to a certain theory, it is believed that, if the BET surface is too high, there are too many pores in the porous dental zirconia article to be sintered. This might negatively influence the sintering of the article and make it more difficult to achieve a dental zirconia article having adequate strength and/or translucency.

If on the other hand the BET surface is too low, it is believed that the porous zirconia article does not have an adequate sintering activity. This might negatively influence the sintering behaviour (e.g. sintering shrinkage, outgassing of remaining sintering aids) of the porous dental zirconia article during the first heat-treating step.

Alternatively, or in addition to the BET surface, the density may also be used for characterizing the material of the porous dental zirconia restoration, because the density is often related to the overall pore volume.

When referring to the BET surface, the surface of the porous zirconia article is meant, not of the powder used for producing the article.

Alternatively, or in addition, the material of the porous dental zirconia article can typically be characterized by the following parameters alone or in combination:
- a) biaxial flexural strength: 15 to 55 determined according to ISO 6872:2015 applying the punch on 3 balls test adapted to measurement in porous state (measurement set up: 3.6 mm punch diameter, 0.1 mm/min load speed, 2 mm sample thickness, support ball diameter 6 mm, 14 mm diameter of supporting balls);
- b) Vickers hardness: 15 to 150 (HV 0.5) or 20 to 140 (HV 0.5);
- c) coefficient of thermal expansion: $8.5*10^{-6}$ $K^{-1}$ to $11.5*10^{-6}$ $K^{-1}$.

The following combination of features is sometimes preferred: a) and b); a) and c); a), b) and c).

If desired, the respective features can be determined as described in the example section.

If the Vickers hardness of the material is too low, the machinability could negatively affect the quality (edge chipping or breaking of the workpiece) as well as in the ease of manual reworking to individualize the frame of a dental restoration or a monolithic restoration as well.

If the Vickers hardness of the material is too high, the wear of the machining tools may increase and shorten tool life to an unacceptable level or the tool could break and destroy the workpiece.

It was found that, if the biaxial flexural strength of the material is too low, the material tends to crack during the milling process, during the manual finishing by a dental technician or during firing.

On the other hand, if the biaxial flexural strength of the material is too high, the processing of the material by a milling machine is often not possible with reasonable efforts. The milling tool used or the milled material may tend to chip or break. In such a case, the shaping of the material had to be done by grinding, e.g. using a Cerec™ grinding machine (Sirona).

The material of the porous dental zirconia article comprises ceramic components and stabilizing components.

Optionally, colouring components and fluorescing components can be present.

The ceramic components are typically selected from oxides of Zr, Hf, Al and mixtures thereof.

Thus, in addition to zirconia, the material of the porous zirconia dental mill blank typically comprises oxides of Hf and optionally Al, typically in only small amounts.

Stabilizing component(s) are typically selected from oxides of Y, Mg, Ca, Ce and mixtures thereof (e.g. $Y_2O_3$, MgO, CaO, $CeO_2$), wherein oxides of Y are often preferred.

If present, colouring component(s) are typically selected from oxides of Fe, Mn, Cr, Ni, Co, Er, Pr, Tb, Nd, in particular selected from the oxides of Mn, Er, Pr, Tb, Co and mixtures thereof (e.g. $MnO_2$, $Er_2O_3$, $Tb_4O_7$, CoO).

If present, the fluorescing agent is typically selected from oxides or hydroxides of Bi and mixtures thereof.

The porous dental zirconia article does typically not contain Eu containing components. It was found that the presence of Eu containing components in the dental zirconia article may sometimes cause undesired effects such as a reddish fluorescence.

Ceramic components are typically present in an amount of 80 to 95 wt. % or 85 to 95 wt. % or 90 to 95 wt. % with respect to the weight of the porous dental mill blank.

Stabilizing components are typically present in an amount of 3 to 12 wt. % or 5 to 10 wt. % or 6 to 10 wt. % with respect to the weight of the porous dental mill blank.

If present, colouring components are typically present in an amount of 0.01 to 2 wt. % or 0.02 to 1.5 wt. % or 0.03 to 1.2 wt. % with respect to the weight of the porous dental mill blank.

If present, the fluorescing agent is typically present in an amount of 0 to 1 wt. % or 0.005 to 0.8 wt. % or 0.01 to 0.1 wt. % with respect to the weight of the porous dental mill blank.

The wt. % are calculated based on the amount of the respective oxides or the ceramic components, stabilizing components, colouring components and fluorescing agents.

For obtaining an aesthetic dental article, the following concentrations were found to be useful:
ceramic components: 80 to 95 wt. % or 85 to 95 wt. %,
stabilizing components: 3 to 12 wt. % or 5 to 11 wt. %,
colouring components: 0 to 2 wt. % or 0.01 to 1.5 wt. %,
fluorescing agent: 0 to 1 wt. % or 0.005 to 0.8 wt. %,
wt. % with respect to the weight of the porous dental mill blank.

According to one embodiment, the material of the porous dental zirconia mill blank is characterized as follows:
$ZrO_2$ content: 70 to 98 mol % or 80 to 97 mol %,
$HfO_2$ content: 0 to 2 mol % or 0.1 to 1.8 mol %,
$Y_2O_3$ content: 1 to 15 mol % or 1.5 to 10 mol % or 2 to 5 mol %,
$Al_2O_3$ content: 0 to 1 mol % or 0.005 to 0.5 mol % or 0.01 to 0.1 mol %.

According to a further embodiment, the material of the porous dental zirconia mill blank is characterized as follows:
$ZrO_2$ content: 90 to 98 mol %,
$HfO_2$ content: 0 to 2 mol %,
$Y_2O_3$ content: 3 to 5 mol %,
$Al_2O_3$ content: 0 to 0.1 mol %.

It was found that a higher $Y_2O_3$ content typically leads to an increase of the cubic crystal phase in the zirconia ceramic material after sintering the material to final density. A higher content of the cubic crystal phase may contribute to a better or higher translucency.

The material of the porous dental zirconia article described in the present text may contain about 3, 4 or 5 mol % yttria. These materials are sometime referred to as 3Y-TZP, 4Y-TZP or 5-YTZP materials.

It has been found that these materials are particularly useful for producing an aesthetic zirconia restoration in a firing process as described in the present text.

In another embodiment, the material of the porous dental zirconia article comprises:
$ZrO_2+HfO_2$: 90 to 95 wt. %;
$Y_2O_3$: 4 to 10 wt. %;
$Al_2O_3$: 0 to 0.15 wt. %;
colouring oxides: 0.01 to 2 wt. %;
wt. % with respect to the weight of the porous dental zirconia article.

There is no need for alumina to be present, however, the presence of a small amount of alumina may be beneficial as it may contribute to a better hydrothermal stability of the zirconia article after sintering.

However, too high an amount of alumina may have a negative impact on the translucency of the zirconia article after sintering.

Thus, alumina may be present in an amount of 0 to 0.15 wt. %, or 0 to 0.12 wt. % or 0 to 0.1 wt. %.

The material of the porous dental zirconia article does typically not comprise the following components alone or in combination before the firing process with the surface treating agent comprising the glass is conducted: glass or glass ceramic; oxides of Si, Fe, K, Na; in an amount above 1 wt. % with respect to the weight of the material of the porous zirconia dental article.

The presence of these elements may negatively affect the overall performance of the porous dental zirconia article during machining or sintering the machined articles.

The firing or sintering of the pre-sintered zirconia article together with the glazing composition can be either done by using a regular sintering protocol or by using a fast-sintering protocol.

A regular sintering protocol is typically characterized as follows:
  sintering temperature: 1,350 to 1,600° C.;
  duration: 50 to 360 min;
  heating rate: 1 to 30° C./min.

A fast sintering protocol is typically characterized as follows:
  sintering temperature: 1,450 to 1,600° C.;
  duration: 10 to 40 min;
  heating rate: 60 to 420° C./min.

A fast-sintering protocol typically comprises the following segments:
  First segment of heat-treating: heating rate of 3 to 7 K/sec; duration: 8 min or less;
  Second segment of heat-treating: heating rate of 0.2 to 1.0 K/sec; duration: 25 min or less;
  Third segment of heat-treating: heating rate of about 0 K/sec; duration: 8 min or less; Cooling-down segment: cooling rate 3 K/sec or more; duration: 6 min or less.

Using a fast-sintering protocol is sometimes preferred, as it allows the production of the dental zirconia restoration in a shorter period of time and with less efforts.

An oven which can be used for the process described in the present text is commercially available from Dentsply Sirona (SpeedFire™).

A suitable furnace is also described in WO 2017/144644 A1 (Sirona). This furnace is for carrying out a heat treatment of a dental replacement part and comprises an induction coil, a radiant heater, an insulation layer and a furnace chamber. Further, the furnace has a cooling system to control the internal temperature of the furnace chamber.

The invention further relates to a dental zirconia restoration which can be obtained or is obtainable by the process described in the present text.

The sintered dental zirconia article obtained by the process described in the present text can typically be characterized by the following features alone or in combination:
  a) density: at least 98.5 (in some embodiments, about 99, 99.5, 99.9, or even at least about 99.99) percent of theoretical density
  b) biaxial flexural strength: 500 to 1,500 MPa or 800 to 1,400 MPa, determined according to ISO 6872:2015;
  c) Vickers hardness: 450 MPa to 2,200 MPa, or 500 MPa to 1,800 MPa HV(2);
  d) phase content tetragonal phase: 10 to 80 wt. % or 20 to 70 wt. % or 40 to 70 wt. %;
  e) phase content cubic phase: 10 to 80 wt. % or 20 to 70 wt. % or 30 to 60 wt. %;
  f) translucency: 25% or more, determined on a sample having a thickness of 1 mm in reflection mode at a wave length of 450 to 800 nm;
  g) being tooth coloured.

A combination of the following features is sometimes preferred: a) and b); a) and c); a), d) and e); or a), b), d), e) and f).

If desired, the respective features can be determined as described in the example section.

These features refer to a dental zirconia article having been sintered without a glazing composition.

The shape of the sintered dental zirconia article is not particularly limited.

The sintered dental zirconia article has typically the shape of a dental bridge, veneer, facing, coping, crown, abutment, monolithic dental restoration or parts thereof.

The invention also relates to a kit of parts.

The kit of parts comprises the glazing composition described in the present text and a dental zirconia mill blank.

The kit of parts is typically provided to the practitioner with an instruction for use.

The instruction for use contains hints or information for what purpose the kit of parts is intended to be used, how the machining should be done and what sintering conditions should be applied.

If desired, the kit of parts may further comprise one or more of the following items:
  sintering aids,
  application device for the surface treating agent,
  optionally a shade guide,
  optionally polishing aids,
  optionally a sintering oven.

Sintering aids include e.g. sintering beads, stands, and other equipment suitable for mechanically supporting the article to be sintered during the sintering process.

Application devices include e.g. brushes, brush pens, sponges, and spray guns.

Further embodiments of the invention are outlined below:

Embodiment 1

A process of producing a dental zirconia restoration, the process comprising the steps of
  providing a porous dental zirconia article as described in the present text,
  applying the glazing composition described in the present text only to at least a part of the surface of the porous dental zirconia restoration,
  sintering the porous dental zirconia article with the glazing composition on its surface to final density,
the porous dental zirconia article being characterized as follows:
  biaxial flexural strength: 15 to 55 determined according to ISO 6872:2015,
  density: from 2.85 to 3.35 g/cm$^3$,
the glazing composition comprising
  liquid: 60 to 90 wt. %,
  glass particles: 9 to 30 wt. %,
  fluorescing component(s) calculated with respect to the amount of europium: 0.1 to 5 wt. %,
  hydrophilic silica nano-particles: 0 to 4 wt. %,
  hydrophobic silica nano-particles: 0 to 5 wt. %,
  wt. % with respect to the weight of the whole composition.

Embodiment 2

A process of producing a dental zirconia restoration, the process comprising the steps of
  providing a porous dental zirconia article as described in the present text,
  applying the glazing composition described in the present text only to at least a part of the surface of the porous dental zirconia restoration, sintering the porous dental zirconia article with the glazing composition on its surface to final density,
the porous dental zirconia article being characterized as follows:
  biaxial flexural strength: 15 to 55 determined according to ISO 6872:2015,
  density: from 2.85 to 3.35 g/cm$^3$,
the glazing composition comprising
  liquid: 60 to 90 wt. %,
  glass particles: 9 to 30 wt. %,
  fluorescing component(s) calculated with respect to the amount of europium: 0.1 to 5 wt. %,
  wt. % with respect to the weight of the whole composition,
  the glass of the glass particles having a viscosity of at least $10^4$ Pa*s at a temperature of 1,300° C.

Embodiment 3

A process of producing a dental zirconia restoration, the process comprising the steps of
  providing a porous dental zirconia article as described in the present text,
  applying the glazing composition described in the present text only to at least a part of the surface of the porous dental zirconia restoration,
  sintering the porous dental zirconia article with the glazing composition on its surface to final density,
the porous dental zirconia article being characterized as follows:
  biaxial flexural strength: 15 to 55 determined according to ISO 6872:2015,
  density: from 2.85 to 3.35 g/cm$^3$,
  coefficient of thermal expansion: $8.5*10^{-6}$ K$^{-1}$ to $11.5*10^{-6}$ K$^{-1}$,
the glazing composition comprising
  liquid: 60 to 90 wt. %,
  glass particles: 9 to 30 wt. %,
  fluorescing component(s) calculated with respect to the amount of europium: 0.1 to 5 wt. %,
  hydrophilic silica nano-particles: 0.1 to 4 wt. %,
  hydrophobic silica nano-particles: 0 to 5 wt. %,
  wt. % with respect to the weight of the whole composition.

Embodiment 4

A process of producing a dental zirconia restoration, the process comprising the steps of
  providing a porous dental zirconia article described in the present text,
  applying the glazing composition described in the present text only to at least a part of the surface of the porous dental zirconia restoration,
  sintering the porous dental zirconia article with the glazing composition on its surface to final density,
the porous dental zirconia article being characterized as follows:
  biaxial flexural strength: 15 to 55 determined according to ISO 6872:2015,
  density: from 2.85 to 3.35 g/cm$^3$,
the glazing composition comprising
  liquid: 60 to 90 wt. %,
  glass particles: 9 to 30 wt. %,
  fluorescing component(s) calculated with respect to the amount of europium: 0.1 to 5 wt. %,
  hydrophilic silica nano-particles: 0 to 4 wt. %,
  hydrophobic silica nano-particles: 0 to 5 wt. %,
  wt. % with respect to the weight of the whole composition.
the sintering being conducted by applying the following conditions:
  sintering temperature: 1,350 to 1,600° C.;
  duration: 50 to 360 min;
  heating rate: 1 to 30° C./min.

Embodiment 5

A process of producing a dental zirconia restoration, the process comprising the steps of
  providing a porous dental zirconia article described in the present text,
  applying the glazing composition described in the present text only to at least a part of the surface of the porous dental zirconia restoration,
  sintering the porous dental zirconia article with the glazing composition on its surface to final density,
the porous dental zirconia article being characterized as follows:
  biaxial flexural strength: 15 to 55 determined according to ISO 6872:2015,
  density: from 2.85 to 3.35 g/cm$^3$,
the glazing composition comprising
  liquid: 60 to 90 wt. %,
  glass particles: 9 to 30 wt. %,
  fluorescing component(s) calculated with respect to the amount of europium: 0.1 to 5 wt. %,
  hydrophilic silica nano-particles: 0 to 4 wt. %,
  hydrophobic silica nano-particles: 0 to 5 wt. %,
  wt. % with respect to the weight of the whole composition.
the sintering being conducted by applying the following conditions:
  sintering temperature: 1,450 to 1,600° C.;
  duration: 10 to 40 min;
  heating rate: 60 to 420° C./min.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate the invention.

EXAMPLES

Unless otherwise indicated, all parts and percentages are on a weight basis, all water is de-ionized water (DI), and all molecular weights are weight average molecular weight. Moreover, unless otherwise indicated, all experiments were conducted at ambient conditions (23° C.; 1013 mbar).

Methods

BET Surface

The BET surface of a porous article is typically determined as follows: Total pore volume and average pore diameter can be analyzed with the use of $N_2$ sorption isotherms and BET surface area analysis. Samples of around 0.1-2 grams were cut if necessary from larger samples in order to be inserted in to the straight tubes. All samples are degassed in vacuum for more than 1 h at 120° C. before analysis. The samples are then analyzed by adsorption and desorption of $N_2$ gas with a Belsorb II (distributed by Robotherm Prazisionsmesstechnik, Bochum, Germany) in a 9 mm cell with 2 cm bulb and with a 5 mm glass rod. At temperature of liquid nitrogen, absorption data points are collected from 0.1 to 0.99 p/p0 and desorption points collected from 0.99 to 0.5 p/p0. The specific surface area S is calculated by the BET method at p/p0 0.25-0.3 (Details see Chapter 12 regarding calculation see Belsorb Analysis Software User Manual Operating Manual, Chapter 12, Bel Japan. INC).

Method for Measuring Translucency (TL)

If desired, the translucency of the ceramic articles can be evaluated with the following procedure: A test piece in the shape of a disc with an approximate thickness of 1±0.05 mm and an area of measurement of at least 12 mm in diameter is provided. For preparation of the test pieces the pre-sintered sample is sawn into wafers with a thickness of approximately 1.3 mm using a dry cut saw. The parallel large faces of the wafer are ground using silicon carbide sand paper (P2500). The ground samples are sintered in an appropriate furnace to a sintered sample with a thickness of 1±0.05 mm. The sintered sample is measured as fired with a spectrophotometer (X-Rite Color i7, Grand Rapids, USA) in reflectance mode against a white and a black background to obtain the opacity of the material. Translucency is calculated according to T=1−opacity. Higher values of translucency are indicative of greater transmission of light, and less opacity.

If desired, L*a*b* values can be determined in addition to opacity using the same equipment.

Particle Size (Suitable for Micro-Sized Particles)

If desired, the particle size distribution including the mean particle size can be determined with a Cilas 1064 (FA. Quantacrome) particle size detection device.

Porosity

If desired, the porosity can be determined as follows: Porosity=(1−(density of porous material/density of sintered material))×100. The density of the porous material can be calculated by the division of weight and volume. Volume can be obtained by geometrical measurements.

Density

If desired, the density of the sintered material can be measured by an Archimedes technique. The measurement is made on a precision balance (e.g. "BP221S" from Sartorius AG, Göttingen, Germany) using a density determination kit (e.g. "YDK01" from Sartorius AG). In this procedure, the sample is first weighed in air (A), then immersed in water (B). The water is a 0.05 wt. % tenside solution (e.g. "Berol 266, Fa. Hoesch). The density is calculated using the formula $\rho=(A/(A-B))\rho 0$, where $\rho 0$ is the density of water. The relative density can be calculated by reference to the theoretical density ($\rho t$) of the material, $\rho_{rel}=(\rho/\rho t)100$.

Viscosity of Glass/Surface Tension

If desired, the viscosity and surface tension of the glass can be calculated using the software tool from SciGlass. In more detail, for calculating the properties of glass compositions described in the present text, the following software tool was used: SciGlass Professional, Version 7.12, Model Priven 2000.

Viscosity of Glazing Composition

If desired, the viscosity of the composition can be determined using a Physica MCR 301 Rheometer (Anton Paar, Graz, Austria) with a cone/plate geometry at a constant shear rate of 616 s' in rotation at 23° C. The diameter of the cone/plate is 25 mm and the gap is set to 0.05 mm.

Determination of Fluorescence

Fluorescence of the glaze of the sintered dental zirconia article was evaluated by the trained eyes of a dental technician under standardized light conditions (light box Spectramax™ III from X-rite, lighting set to UV ultraviolet).

Determination of Homogeneity of Glazing Composition and Sintered Zirconia Article If desired, the homogeneity (e.g. the presence of air bubbles) of the sintered glaze can be analyzed by darkfield illumination microscopy.

Materials

TABLE 1

| Component | Description | Source |
|---|---|---|
| Glycerol | Liquid | Aldrich |
| HDK ™-H2000 | Silanized fumed silica | Wacker |
| Aerosil ™ Ox50 | Non-silanized fumed silica | Evonik |
| E142 | Color component (food color) | |
| E131 | Color component (food color) | |
| G1 | Experimental glass | 3M Oral Care |
| G3 | Experimental glass | 3M Oral Care |
| Xanthan | Rheological additive | |
| 4Y-TZP | Porous zirconia sample | 3M Oral Care |
| Europium (III) oxide | Fluorescing agent | Sigma Aldrich |
| Terbium (III, IV) oxide | Fluorescing agent | Sigma Aldrich |
| Cerium (IV) oxide | Fluorescing agent | Sigma Aldrich |
| Dysprosium (III) oxide | Fluorescing agent | Sigma Aldrich |
| F-X-2 | Ce/Tb doped $Y_2SiO_5$, fluorescent tooth pigment | Chemichl |

Preparation Method for Glazing Composition

The components of the composition were mixed using a magnetic stirrer.

Preparation Method for Glass

Glass powders G1/G2/G3 were produced as follows: The respective oxides were weighed and filled into a PP bottle. IPA was added until a slurry was obtained. Zirconia milling media was added, and the mixtures were rolled on a roller mill over-night. The mixture was screened into a plastic petry dish and dried. The dried powder was filled into an alumina crucible and calcined at 800° C. for 2 hrs. The calcined powder was filled into a Pt/Rh crucible, heated to 1650° C., and held at 1650° C. for 2 hrs. The molten glass was cooled quickly by quenching in DI water. The glass was crushed and ball milled to obtain a milled glass powder with a mean particle size of 2.5 μm.

The Glass Powders used had the following composition and properties:

TABLE 2

| | G1 | G2 | G3 |
|---|---|---|---|
| $SiO_2$ | 93 mol % | 90 mol % | 92.3 mol % |
| $B_2O_3$ | 5 mol % | 10 mol % | — |
| $Al_2O_3$ | 2 mol % | — | 2.5 mol % |
| MgO | — | — | 2.5 mol % |
| $K_2O$ | — | — | 2.5 mol % |
| $Eu_2O_3$ | — | — | 0.2 mol % |

TABLE 2-continued

|  | G1 | G2 | G3 |
|---|---|---|---|
| Viscosity at 1,300° C.** | $10^{6.3}$ | $10^{6.3}$ | $10^{4.7}$ |
| Viscosity at 1,600° C.** | $10^{3.9}$ | $10^{5.5}$ | $10^{2.3}$ |

**Calculated and given in Pa*s

Preparation Method for Zirconia Article

Mill blank samples were produced from a 4Y-TZP powder with the following composition: $ZrO_2$: 90.71 wt. %; $Y_2O_3$: 7.24 wt. %, $Al_2O_3$: 0.06 wt. %.

The following steps were applied: Filling the powder composition in a mould; applying pressure (200 MPa) to the powder filling; demoulding the compacted body; applying a heat treatment at 970° C. for about 2 hours. Platelets were cut from the heat-treated mill blank samples (dimensions 19.5 mm×39.5 mm×16.0 mm) to a thickness of 1.3 mm.

Application Method

The composition to be tested was applied onto ½ of the surface of the porous zirconia sample platelet with a brush. The platelet was allowed to dry for 3 min and was then placed into a speed-firing furnace (Dentsply Sirona).

Firing Process A—Regular Glaze Firing Process

The surface-treated test samples were heat-treated according to the following firing protocol using a dental furnace Austromat™ (Dekema).

Heating conditions: Pre-heating of dental furnace to 500° C.; 500° C.-900° C.; 1.5° C./s; 180s hold.

Firing Process B—Fast-Firing Process

The surface-treated test samples were heat-treated according to the following sinter protocol using a CEREC Speed-Fire™ furnace from Dentsply Sirona.

| RT-400° C.: | heating rate: 5.3° C./s |
| 400° C.-1350° C.: | heating rate: 5.3° C./s |
| 1350° C.-1580° C.: | heating rate: 0.5° C./s; 120 s hold |
| 1580° C.-1000° C.: | heating rate: −3.2° C./s; 10 s hold |
| 1000° C.-950° C.: | heating rate: −0.3° C./s |

After cooling, the samples were investigated with respect to fluorescence.

Inventive Example 1 (Eu Ions in Eu Compound)

A slurry was made by mixing 3.500 g glycerol, 0.015 g silanized fumed silica (HDK-H2000), <0.001 g color E142, 0.020 g europium(III) oxide and 1.465 g G1 glass particles. The viscosity of this composition was measured to be 1,172 mPa*s.

The slurry was applied as described in the application method and the then sintered using Firing Process B. The resulting glaze was translucent and displayed clearly visible blue fluorescence under UV light.

Inventive Example 2 (Eu Ions in Glass Particles)

A slurry was made by mixing 18.000 g of deionized water, 0.075 g xanthan, 0.001 g color E142 and 1.924 g G3 glass particles. The viscosity of this composition was measured to be 20 mPa*s. The slurry was applied as described in the application method and the then sintered using Firing Process B. The resulting glaze was translucent and displayed clearly visible blue fluorescence under UV light.

Inventive Example 3 (Eu Ions in Glass Particles)

A slurry was made by mixing 18.000 g of deionized water, 0.075 g xanthan, 0.074 g un-silanized fumed silica (Ox50), 0.001 g color E131 and 1.850 g G3 glass particles. The viscosity of this composition was measured to be 19 mPa*s. The slurry was applied as described in the application method and the then sintered using Firing Process B. The resulting glaze was translucent and displayed clearly visible blue fluorescence under UV light.

Inventive Example 4 (Eu/Dy Ions in Eu and Dy Compounds)

A slurry was made by mixing 3.500 g glycerol, 0.010 g silanized fumed silica (HDK-H2000), <0.001 g color E142, 0.015 g europium(III) oxide, 0.015 g dysprosium(III) oxide and 1.460 g G1 glass particles. The viscosity of this composition was measured to be 1,538 mPa*s. The slurry was applied as described in the application method and the then sintered using Firing Process B. The resulting glaze was translucent and displayed clearly visible blue/violet fluorescence under UV light.

Inventive Example 5 (Eu-Ions in Glass Particles)

A slurry was made by mixing 2 g of Isopropyl alcohol with 1 g of G3 glass powder in a glass vial. The vial was closed and the particles were sonically dispersed for 5 min. The viscosity of the composition was not measured. The slurry was filled into a spray device and sprayed unto the surface of the porous zirconia sample and then sintered using Firing Process B. The resulting glaze was translucent and displayed clearly visible blue/violet fluorescence under UV light.

Comparative Example 1 (Ce/Tb Pigment)

A slurry was made by mixing 4.500 g of deionized water, 0.020 g xanthan, <0.001 g food color E142, 0.015 g fluorescent tooth pigment F-X-2 and 0.465 g G1 glass particles. The slurry was applied as described in the application method and the then sintered using Firing Process A. The resulting glaze was not translucent but displayed clearly visible blue fluorescence under UV light. The same sample was fired again according to Firing Process B. The resulting glaze was translucent and displayed no fluorescence under UV light.

Comparative Example 2 (Ce/Tb Ions in Ce and Tb Compounds)

A slurry was made by mixing 3.500 g glycerol, 0.050 g silanized fumed silica (HDK-H2000), <0.001 g color E142, 0.005 g cerium(IV) oxide, 0.015 g terbium(III, IV) oxide and 1.430 g G1 glass particles. The slurry was applied as described in the application method and the then sintered using Firing Process B. The resulting glaze was translucent and displayed no visible fluorescence under UV light.

Comparative Example 3 (DV Ions in Dy Compound)

A slurry was made by mixing 4.500 g of deionized water, 0.020 g xanthan, <0.001 g food color E142, 0.020 g dysprosium(III) oxide and 0.460 g G1 glass particles. The slurry was applied as described in the application method and the then sintered using Firing Process B. The resulting glaze was translucent and displayed no visible fluorescence under UV light.

Compositions and Results

TABLE 3

|  | solvent | xanthan | silanized silica | non-silanized silica | glass | fluorescence additive(s) | firing process | fluorescence after firing |
|---|---|---|---|---|---|---|---|---|
| I.E. 1 | 70.0 | — | 0.3 | — | 29.3 | 0.4 (Eu) | B | blue |
| I.E. 2 | 90.0 | 0.4 | — | — | 9.6 | — | B | blue |
| I.E. 3 | 90.0 | 0.4 | — | 0.4 | 9.2 | — | B | blue |
| I.E. 4 | 70.0 | — | 0.2 | — | 29.2 | 0.3 (Eu) + 0.3 (Dy) | B | blue/violet |
| I.E. 5 | 67 | — | — | — | 33 | — | B | blue |
| C.E. 1 (A) | 90.0 | 0.4 | — | — | 9.3 | 0.3 (pigment) | A | blue |
| C.E. 1 (B) | 90.0 | 0.4 | — | — | 9.3 | 0.3 (pigment) | B | none |
| C.E. 2 | 70.0 | — | 1.0 | — | 28.6 | 0.1 (Ce) + 0.3 (Tb) | B | none |
| C.E. 3 | 90.0 | 0.4 | — | — | 9.2 | 0.4 (Dy) | B | none |

Amounts are given in wt. %

Eu ions add fluorescence to the glaze that is desirable in color and intensity.

The state-of-the-art fluorescence pigment F-X-2 does not survive a 1,580° C. sintering process.

The combination of the ions Ce/Tb was expected to yield tooth-like fluorescence as is does in the fluorescence pigment, but it does not.

Use of Dy ions in addition to Eu ions slightly changes the fluorescence color.

Use of Dy ions alone yields no fluorescence.

The invention claimed is:

1. A glazing composition for a porous dental zirconia article, the glazing composition comprising
    liquid,
    glass particles present in an amount of 5 wt % to 40 wt % with respect to the weight of the glazing composition, wherein if the glass particles comprise $Li_2O$, the $Li_2O$ is present in an amount of no more than 0.1 mol %,
    fluorescing component(s) comprising europium,
        wherein the fluorescing component(s) can be contained in the glass particles or as separate component,
    optionally hydrophilic silica nano-particles, and
    optionally hydrophobic silica nano-particles.

2. The glazing composition according to claim 1, the ratio of glass particles to europium being in a range of 1,000:1 to 20:1 with respect to weight.

3. The glazing composition according to claim 1, the liquid selected from water, alcohols, polyols, and a combination thereof.

4. The glazing composition according to claim 1, the glass particles comprising one or more of the following compositions:

|  | 1 | 2 | 3 | 4 | 5 | 6 | 7 |
|---|---|---|---|---|---|---|---|
| $SiO_2$ | 80 to 98 | 80 to 98 | 80 to 98 | 80 to 98 | 80 to 98 | 85 to 98 | 80 to 98 |
| $B_2O_3$ | 0 to 15 | 0 to 15 | 2 to 15 |  |  | 2 to 15 |  |
| $Na_2O$ | 0 to 5 | 0 to 5 |  |  |  |  |  |
| $K_2O$ | 0 to 5 | 0 to 5 |  | 0.1 to 5 | 0.1 to 5 |  | 5 to 10 |
| $Al_2O_3$ | 0 to 5 | 0 to 5 | 0.1 to 5 | 0.1 to 5 | 0.1 to 5 |  | 8 to 12 |
| $La_2O_3$ | 0 to 1 | 0 to 1 |  |  |  |  |  |
| MgO | 0 to 5 | 0 to 5 |  | 0.1 to 5 | 0.1 to 5 |  |  |
| CaO | 0 to 2 | 0 to 2 |  |  |  |  |  |
| SrO | 0 to 2 | 0 to 2 |  |  |  |  |  |
| BaO | 0 to 2 | 0 to 2 |  |  |  |  |  |
| $Bi_2O_3$ | 0 to 0.5 | 0 to 0.5 |  |  |  |  |  |
| $Eu_2O_3$ | 0 to 1 | 0.05 to 1 |  |  | 0 to 1 |  |  | wherein the amounts are given in mol %.

5. The glazing composition according to claim 4, the glass particles being characterized by one or more of:
    viscosity: at least $10^4$ Pa*s at a temperature of 1,300° C.;
    coefficient of thermal expansion: $1*10^{-6}$ $K^{-1}$ to $10*10^{-6}$ $K^{-1}$;
    surface tension: of 210 to 300 mN/m at 1,300° C.;
    Littleton softening point viscosity at a temperature of 1,100° C. to 1,350° C.;
    flow point viscosity at a temperature of 1,300° C. to 1,650° C.; and
    particle size ($D_{50}$): 1 to 40 μm,
    wt. % with respect to the weight of the glazing composition.

6. The glazing composition according to claim 1, the fluorescing component(s) characterized by one or more of:
    being present in an amount of 0.1 to 5 wt. % with respect to the weight of the whole composition calculated with respect to the amount of europium;
    particle size ($D_{50}$): 1 to 40 μm; and
    being selected from oxides, hydroxides or carbonates of Eu.

7. The glazing composition according to claim 1, comprising:
    the liquid present in an amount of 50 to 95 wt. %,
    the fluorescing component(s) present in an amount of 0.1 to 5 wt. % calculated with respect to the amount of europium,
    the hydrophilic silica nano-particles present in an amount of 0 to 5 wt. %, and
    the hydrophobic silica nano-particles present in an amount of 0 to 5 wt. %; and further comprising:
    a rheological additive present in an amount of 0 to 1 wt. %,
    an organic colorant present in an amount of 0 to 0.5 wt. %,
    wt. % with respect to the weight of the glazing composition.

8. The glazing composition according to claim 1, comprising hydrophilic silica nano-particles, the hydrophilic silica nano-particles being characterized by one or more of:
  particle size ($D_{50}$): 10 to 70 nm;
  BET surface: 20 to 500 $m^2/g$; and
  being present in an amount of 0.1 to 5 wt. %,
  wt. % with respect to the weight of the glazing composition.

9. The glazing composition according to claim 1, being characterized by one or more of:
  viscosity: 10 to 2,500 mPa*s at 23° C.; and
  pH value: 6 to 9.

10. The glazing composition according to claim 1, wherein:
  the liquid is selected from water, an alcohol, a polyol, and a combination thereof,
  the liquid is present in an amount of 50 to 95 wt. %,
  the glass particles are characterized by a particle size ($D_{50}$) of 1 to 40 μm
  the glass particles characterized by a viscosity of $10^4$ to $10^7$ Pa*s at 1,300° C.,
  the fluorescing component(s) is present in an amount of 0.1 to 5 wt. % calculated with respect to the amount of europium,
  the hydrophilic silica nano-particles are present in an amount of 0 to 5 wt. %, and
  the hydrophobic silica nano-particles are present in an amount of 0 to 5 wt. %,
  wt. % with respect to the weight of the glazing composition.

11. The glazing composition of claim 1, the glass particles comprising $SiO_2$ in an amount of at least 80 wt %.

12. The glazing composition of claim 1, the glass particles characterized by a particle size ($D_{50}$) of 1 to 40 μm.

13. The glazing composition of claim 1, wherein the fluorescing component(s) comprising europium is europium oxide, the fluorescing component(s) comprising europium present in an amount of 0.1 to 5 wt. % calculated with respect to the weight of europium.

14. A glazing composition for a porous dental zirconia article, the glazing composition comprising liquid,
  glass particles comprising at least 80 wt. % $SiO_2$,
  fluorescing component(s) comprising europium,
    wherein the fluorescing component(s) can be contained in the glass particles or as separate component,
  optionally hydrophilic silica nano-particles, and
  optionally hydrophobic silica nano-particles.

15. A process of producing a dental zirconia article, the process comprising:
  providing a porous dental zirconia article,
  applying the glazing composition according to claim 1 to at least a part of a surface of the porous dental zirconia article, and
  sintering the porous dental zirconia article with the glazing composition on the surface to final density.

16. The process according to claim 15, the porous dental zirconia article being characterized by one or more of:
  biaxial flexural strength: 15 to 55 determined according to ISO 6872:2015; and
  Vickers hardness: 15 to 150 (HV 0.5).

17. The process according to claim 15, the sintering comprising regular sintering or fast sintering,
  the regular sintering comprising one or more of:
    sintering temperature: 1,350 to 1,600° C.;
    duration: 50 to 360 min; and
    heating rate: 1 to 30° C./min;
  the fast sintering comprising one or more of:
    sintering temperature: 1,450 to 1,600° C.;
    duration: 10 to 40 min; and
    heating rate: 60 to 420° C./min.

18. A kit of parts comprising:
  the glazing composition according to claim 1; and
  a dental zirconia mill blank suitable for producing a dental restoration.

19. The kit of claim 18, further comprising one or more of:
  sintering aids,
  application device for the surface treating agent,
  a shade guide,
  polishing aids, and
  a sintering oven.

* * * * *